United States Patent [19]

Boone

[11] 4,153,054

[45] May 8, 1979

[54] TUBULAR SURGICAL DRAPE

[75] Inventor: Walter S. Boone, Valdese, N.C.

[73] Assignee: Alba-Waldensian, Incorporated, Valdese, N.C.

[21] Appl. No.: 848,399

[22] Filed: Nov. 4, 1977

[51] Int. Cl.² ............................................. A61F 13/00
[52] U.S. Cl. ................................. 128/132 D; 223/111; 128/157
[58] Field of Search ............... 128/132 D, 132 R, 157, 128/165, 294, 168, 295, 282; 223/111, 112

[56] References Cited

U.S. PATENT DOCUMENTS

| 3,097,644 | 7/1963 | Parker | 128/157 |
| 3,968,792 | 7/1976 | Small | 128/132 D |

FOREIGN PATENT DOCUMENTS 2410697  3/1974  Fed. Rep. of Germany ........... 128/294

*Primary Examiner*—Dalton L. Truluck
*Assistant Examiner*—Milford Juten
*Attorney, Agent, or Firm*—Bell, Seltzer, Park & Gibson

[57] ABSTRACT

The tubular surgical drape is adapted to cover a patient extremity and includes a pull sleeve concentrically rolled with a tubular stockinette to form a doughnut-shaped roll. The pull sleeve surrounds the outer wall of the doughnut-shaped roll and applies an unrolling force in a uniform manner completely around the rolled stockinette so as to provide for rapid and uniform application of the tubular stockinette to the patient extremity. Rupturable means, in the form of one or more tear lines, is provided along the length of the pull sleeve to provide for easy separation while the pull sleeve is being drawn along the patient extremity to unroll and apply the stockinette thereto.

8 Claims, 7 Drawing Figures

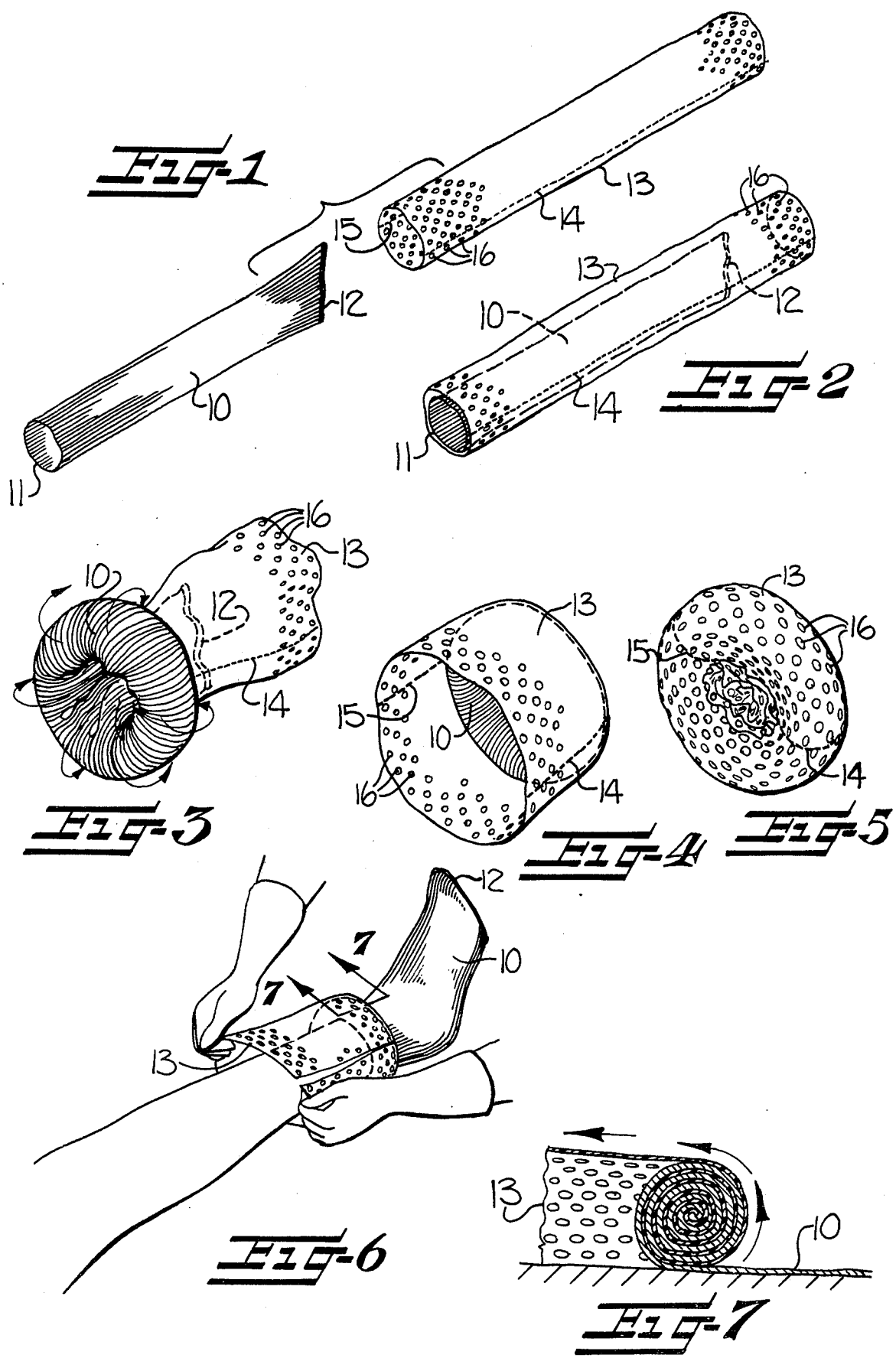

TUBULAR SURGICAL DRAPE

This invention relates generally to a tubular surgical drape of the type adapted to be positioned on and surround a patient extremity, and more particularly to a drape which includes a rolled tubular stockinette and a pull sleeve surrounding and concentrically rolled with the stockinette for uniformly unrolling the stockinette onto the patient extremity.

It is a common practice in performing surgical operations on a patient extremity, such as a limb, to cover the limb with a tubular drape commonly known as a stockinette. The stockinette material is usually formed of tubular knit cotton yarn and is normally provided in various diameters and in rolls of various lengths. The stockinette is provided with a closed end and is rolled into a doughnut shape with the closed end in the center. To position the stockinette on the limb, the closed end is positioned over the end of the extremity or limb and the stockinette is manually unrolled along the extremity to cover the same. This manual unrolling of the stockinette is a relatively slow process and can cause contamination of the sterile stockinette.

In an attempt to solve this problem, U.S. Pat. No. 3,968,792 to Martin H. Small, issued July 13, 1976, discloses a rolled tubular surgical drape with narrow pull straps concentrically rolled along opposite sides of a stockinette to provide means for unrolling the stockinette along the patient extremity. However, the narrow pull straps disclosed in this patent provide very narrow areas of unrolling force at opposite sides of the stockinette, making it difficult to uniformly unroll the stockinette onto the patient extremity. Also, the narrow pull straps may become broken when being used to unroll the stockinette.

With the foregoing in mind, it is an object of the present invention to provide a tubular surgical drape which includes a rolled tubular stockinette having a closed end positioned in the center thereof and a pull sleeve concentrically rolled with the stockinette so that the pull sleeve applies uniform force completely around the rolled stockinette as the pull sleeve is drawn along the patient extremity to unroll and apply the tubular stockinette to the patient extremity.

In accordance with the present invention, the pull sleeve is in the form of a thin tube of fluid impervious material, such as polyethylene, and is provided with perforations extending longitudinally thereof to permit sterilization of the rolled tubular surgical drape. The pull sleeve includes rupturable means extending along the length of the pull sleeve to provide for easy separation when the pull sleeve is being drawn along the patient extremity to unroll and apply the tubular stockinette thereto. The rupturable means preferably includes one or more periodically interrupted cut lines extending longitudinally along the pull sleeve to provide tear lines for easy separation of the pull sleeve.

The tubular stockinette is concentrically rolled with the pull sleeve to form a doughnut-shaped roll with the closed end of the tubular stockinette extending across one end portion of the doughnut-shaped roll. The pull sleeve is wrapped around the outer surface of the doughnut-shaped roll with the free end of the pull sleeve being tucked into the opening in the doughnut-shaped roll. To apply the stockinette to the patient, the free end of the pull sleeve is withdrawn from the opening in the doughnut-shaped roll and drawn upwardly along the patient extremity so that an unrolling force is applied in a uniform manner completely around the roll and the stockinette is unrolled onto the patient extremity in a uniform manner.

Other objects and advantages will appear as the description proceeds when taken in connection with the accompanying drawings, in which FIG. 1 is an isometric view of the tubular stockinette and pull sleeve of the present invention longitudinally aligned and in preparation for the formation of the surgical drape;

FIG. 2 is a view similar to FIG. 1 but showing the pull sleeve drawn over and surrounding the tubular stockinette;

FIG. 3 is an isometric view illustrating the manner in which the tubular stockinette is outwardly rolled to form a doughnut-shaped roll with the closed end in the center thereof and with the free end of the pull sleeve extending outwardly therefrom;

FIG. 4 is a view similar to FIG. 3 but illustrating the free end of the pull sleeve being wrapped around and surrounding the outer surface of the doughnut-shaped roll and extending outwardly therefrom;

FIG. 5 is a view similar to FIG. 4 but illustrating the free end of the pull sleeve being tucked into the center of the doughnut-shaped roll;

FIG. 6 is a perspective view illustrating the tubular surgical drape of the present invention being applied to a patient's leg by drawing the free end of the pull sleeve upwardly along the leg; and FIG. 7 is an enlarged vertical sectional view taken substantially along the line 7—7 in FIG. 6 and illustrating the manner in which the pull sleeve is concentrically rolled with the stockinette.

As illustrated in the drawings, the tubular surgical drape of the present invention includes a tubular knit stockinette 10 having inner and outer walls, an open end 11 and a closed end 12. The end 12 may be closed by any suitable means such as an overedge seam or the like. The tubular surgical drape of the present invention also includes a pull sleeve 13 which is formed of a fluid impervious thin tubular material, such as polyethylene. The pull sleeve 13 includes rupturable means extending longitudinally thereof so that the pull sleeve will separate longitudinally when being drawn along the patient extremity to unroll and apply the tubular stockinette thereto. The pull sleeve rupturable means is illustrated as including a pair of periodically interrupted cut lines 14, 15 extending longitudinally along opposite sides of the pull sleeve 13 to provide tear lines. A plurality of perforations 16 are spaced along the length of the pull sleeve 13 to facilitate sterilization of the surgical drape when in rolled condition.

To form the surgical drape in accordance with the present invention, it is preferred that the pull sleeve 13 be drawn over one end of the tubular stockinette 10 so that one end is substantially aligned with the open end 11 of the stockinette. The other end of the pull sleeve 13 extends outwardly beyond the closed end 12 of the stockinette 10, as shown in FIG. 2. The open end of the stockinette 11 is then curled outwardly from the center thereof and rolled toward the closed end 12, thereby concentrically rolling the pull sleeve 13 with the tubular stockinette, in the manner illustrated in FIG. 3, to form a doughnut-shaped roll. Rolling continues until the closed end 12 of the stockinette 10 is positioned in the center of the doughnutshaped roll the free end portion of the pull sleeve 13 extending outwardly therefrom. The free end portion of the pull sleeve 13 is then wrapped around the outer surface of the doughnut-shaped roll, as shown in FIG. 4, and the free end is tucked into the opening in the doughnut-shaped roll, as illustrated in FIG. 5.

The tubular surgical drape of the present invention has been illustrated and described as being formed by initially placing the pull sleeve 13 over and surrounding the outer wall of the stockinette 10 and then rolling the stockinette 10 and pull sleeve 13 outwardly and toward the closed end 12 of the stockinette. However, the pull sleeve 13 may be initially placed inside of the stockinette 10 and concentrically rolled therewith. In this instance, it is preferred that an excess length of the pull sleeve 13 be provided in the inside of the closed end 12. Upon completion of the rolling step this excess length of the pull sleeve 13 provides a free end positioned in the center of the doughnut-shaped roll and this free end will be available to be drawn along the patient extremity to unroll and apply the stockinette thereto.

The rolled tubular surgical drape may then be placed into a suitable package which may include an indication of the size and type of the tubular surgical drape contained therein, such as the diameter and the length. The package, not shown, may be sterilized and the perforations 16 in the pull sleeve 13 permit penetration of the sterilization medium into the tubular surgical drape rolled therein.

When the rolled tubular surgical drape is to be drawn onto and surround a patient extremity, such as the leg illustrated in FIG. 6, the free end of the pull sleeve 13 is removed from the center of the doughnutshaped roll and placed over the toes. The free end of the pull sleeve 13 is drawn upwardly along the leg to unroll and apply the tubular stockinette 10 thereto. As the free end of the pull sleeve 13 is drawn upwardly, the periodically interrupted cut lines 14, 15 permit opposite halves of the pull sleeve 13 to separate and an unrolling force is applied to the rolled stockinette in a uniform manner completely around the rolled stockinette so that it is unrolled in a uniform manner and may be rapidly applied to the leg. The manner in which the uniform force is applied completely around the rolled stockinette is best illustrated in FIG. 7, indicating that an upward force applied to the pull sleeve 13 uniformly unrolls the rolled stockinette 10 along the leg of the patient. When the stockinette 10 is completely unrolled, the separated halves of the pull sleeve 13 may be discarded.

In the drawings and specification, there has been set forth a preferred embodiment of the invention, and although specific terms are employed, they are used in a generic and descriptive sense only and not for purposes of limitation, the scope of the invention being defined in the claims.

That which is claimed is:

1. A tubular surgical drape adapted to be drawn onto and surround a patient extremity and comprising
   (a) a tubular stockinette having inner and outer walls, an open end and a closed end, said tubular stockinette having the open end curled outwardly from the center thereof and rolled toward the closed end, and
   (b) a pull sleeve concentrically rolled with said tubular stockinette, said pull sleeve including rupturable means extending longitudinally and substantially throughout the length thereof so that said pull sleeve will readily separate longitudinally when said pull sleeve is being drawn along the patient extremity to unroll and apply the tubular stockinette thereto.

2. A tubular surgical drape according to claim 1 wherein said rupturable means extends along opposed sides of said pull sleeve.

3. A tubular surgical drape according to claim 1 wherein said pull sleeve comprises thin tubular material and wherein said pull sleeve includes a plurality of perforations spaced along the length thereof to facilitate sterilization of said surgical drape.

4. A tubular surgical drape according to claim 1 wherein said pull sleeve rupturable means comprises periodically interrupted cut lines extending longitudinally along opposite sides of said pull sleeve and forming tear lines.

5. A tubular surgical drape according to claim 1 wherein said tubular stockinette comprises a seamless knit fabric.

6. A tubular surgical drape according to claim 1 wherein said concentrically rolled tubular stockinette and pull sleeve form a doughnutshaped roll with the closed end of said tubular stockinette extending across one end portion of said doughnut-shaped roll, and wherein said pull sleeve is wrapped around the outer surface of said doughnut-shaped roll with the free end being tucked into the opening in said doughnut-shaped roll.

7. A tubular surgical drape adapted to be drawn onto and surround a patient extremity and comprising
   (a) a tubular stockinette comprising seamless knit fabric having inner and outer walls, an open end and a closed end, said tubular stockinette having the open end curled outwardly from the center thereof and rolled toward the closed end, and
   (b) a pull sleeve of thin tubular material concentrically rolled with said tubular stockinette, said pull sleeve including rupturable means extending longitudinally along opposed sides thereof for easy separation so that opposite halves of said pull sleeve will separate longitudinally when being drawn along the patient extremity to unroll and apply the tubular stockinette thereto, and said pull sleeve including a plurality of perforations spaced along the length thereof to facilitate sterilization of said surgical drape when in rolled condition.

8. A tubular surgical drape according to claim 7 wherein said pull sleeve rupturable means comprises periodically interrupted cut lines extending longitudinally along opposite sides of said pull sleeve and forming tear lines.

* * * * *